US007833540B2

(12) United States Patent
Damiani et al.

(10) Patent No.: US 7,833,540 B2
(45) Date of Patent: Nov. 16, 2010

(54) SYNTHESIS OF A NITROXIDE ANTIOXIDANT AND METHODS OF USE IN COSMETIC AND DERMATOLOGICAL COMPOSITIONS

(75) Inventors: Elisabetta Damiani, Cagli (IT); Paola Astolfi, Mogliano (IT); Lucedio Greci, Felino (IT)

(73) Assignee: Jarrow Formulas, Inc., Los Angeles, CA (US)

( * ) Notice: Subject to any disclaimer, the term of this patent is extended or adjusted under 35 U.S.C. 154(b) by 683 days.

(21) Appl. No.: 11/640,158

(22) Filed: Dec. 15, 2006

(65) Prior Publication Data

US 2007/0140996 A1    Jun. 21, 2007

Related U.S. Application Data

(60) Provisional application No. 60/750,584, filed on Dec. 15, 2005.

(51) Int. Cl.
*A61K 8/02* (2006.01)
*A61K 1/08* (2006.01)
*C07D 211/40* (2006.01)

(52) U.S. Cl. .................... 424/401; 424/59; 546/216
(58) Field of Classification Search ................ 424/401
See application file for complete search history.

(56) References Cited

U.S. PATENT DOCUMENTS

| 4,970,332 | A | * | 11/1990 | Caskey | ............. 560/104 |
| 5,002,760 | A | * | 3/1991 | Katzev | ............. 424/59 |
| 5,059,689 | A | | 10/1991 | Rody et al. | |
| 5,679,691 | A | | 10/1997 | Ribier et al. | |
| 6,004,558 | A | * | 12/1999 | Thurn et al. | ............. 424/757 |
| 2003/0224026 | A1 | | 12/2003 | Greci et al. | |
| 2005/0276762 | A1* | | 12/2005 | Das et al. | ............. 424/59 |
| 2006/0252857 | A1* | | 11/2006 | Schafer et al. | ............. 524/100 |

FOREIGN PATENT DOCUMENTS

GB    2 149 789    6/1985

OTHER PUBLICATIONS

J.K. Broadbent, B.S. Martincigh, M.W. Raynor, L.F. Salter, R. Moulder, P. Sjoberg, K.E. Markides, Capillary supercritical fluid chromatography combined with atmospheric pressure chemical ionisation mass spectrometry for the investigation of photoproduct formation in the sunscreen absorber 2-ethylhexyl-p-methoxycinnamate, J. Chromatography A, 732.*

(Continued)

*Primary Examiner*—Sharmila Gollamudi Landau
*Assistant Examiner*—Nicoletta Kennedy
(74) *Attorney, Agent, or Firm*—McCarter & English, LLP

(57) ABSTRACT

The present invention provides a dermatological and/or cosmetic composition which includes a methoxycinnamate, and a cyclic nitroxide. The present invention further provides a method of synthesizing photo absorbing-antioxidant compounds and their use in dermatological and/or cosmetic compositions. In addition, the present invention relates to the use of methoxycinnamate, and nitroxide compounds for the preparation of a composition for the dermatological and/or cosmetic treatment of skin.

3 Claims, 3 Drawing Sheets

OTHER PUBLICATIONS

E. Damiani, L. Greci, R. Parsons, J. Knowland, Nitroxide radicals protect DNA from damage when illuminated in vitro in the presence of dibenzoylmethane and a common sunscreen ingredient, Free Radic. Biol. Med. 26 (1999) 809-816.*

Rozantsev et al., Stable Esters and Amides of 2,2,6,6,-tetramethyl-1-oxyl-4-piperidine with Carboxylic Acids, Izv. Akad. Nauk SSSR, Ser. Khim., 2106, 1968.*

Lee et al. Cytotoxicity of phenolic acid phenethyl esters on oral cancer cells. Cancer Letters 223 (2005) 19-25. Published Jun. 2, 2005.*

Broadbent et al., Capillary supercritical fluid chromatography combined with atmospheric pressure chemical ionisation mass spectrometry for the investigation of photoproduct formation in the sunscreen absorber 2-ethylhexyl-p-methoxycinnamate, J. Chromatography A, 732, p. 101-110. Published 1996.*

Damiani et al., Nitroxide radicals protect DNA from damage when illuminated in vitro in the presence of dibenzoylmethane and a common sunscreen ingredient, Free Radic. Biol. Med. 26 (1999) 809-816.*

Rozantsev et al., Stable Esters and Amides of 2,2,6,6,-tetramethyl-1-oxyl-4-piperidine with Carboxylic Acids, Izv. Akad. Nauk SSSR, Ser. Khim., 2106, 1968.*

J.M. Allen, C.J. Gosset, A.K. Allen, Photochemical formation of singlet molecular oxygen in illuminated aqueous solutions of several commercially available sunscreen ingredients, Chem. Res. Toxicol. 9 (1996) 605-609.

I. Andrae, A. Bringhen, F. Boehm, H. Gonzenbach, T. Hill, L. Mulroy, T.G. Truscott, A UVA filter (4-tert-butyl-4-methoxydibenzoylmethane): photoprotection reflects photophysical properties, J. Photochem. Photobiol. B. 37 (1997) 147-150.

T. Armeni, E. Damiani, M. Battino, L. Greci, G. Principato, Lack of in vitro protection by a common sunscreen ingredient on UVA-induced cytotoxicity in keratinocytes, Toxicology, 203 (2004) 165-178.

E.F. Bernstein, S.K. Kong, D.B. Brown, B.C. Kwak, T. Takeuchi, F.P. Gasparro, J. Uitto, The nitroxide TEMPOL affords protection against ultraviolet radiation in a transgenic murine fibroblast culture model of cutaneous photoaging, Exp. Dermatol., 10 (2001) 55-61.

J.K. Broadbent, B.S. Martincigh, M.W. Raynor, L.F. Salter, R. Moulder, P. Sjoberg, K.E: Markides, Capillary supercritical fluid chromatography combined with atmospheric pressure chemical ionisation mass spectrometry for the investigation of photoproduct formation in the sunscreen absorber 2-ethylhexyl-p-methoxycinnamate, J. Chromatography A, 732 (1996) 101-110.

J. Buege, S.D. Aust, Microsomal lipid peroxidation, Methods Enzymol. 52 (1978) 302-310.

A. Cantrell, D.J. McGarvey, Photochemical studies of 4-tert-buty1-4-methoxydibenzoylmethane (BM-DBM), J. Photochem. Photobiol. B. 64 (2001) 117-122.

E. Damiani, P. Carloni, C. Biondi, L. Greci, Increased oxidative modification of albumin when illuminated in vitro in the presence of a common sunscreen ingredient: protection by nitroxide radicals, Free Radic. Biol. Med. 28 (2000) 193-201.

E. Damiani, R. Castagna, L. Greci, The effects of derivatives of the nitroxide TEMPOL on UVA-mediated in vitro lipid and protein oxidation, Free Radic. Biol. Med. 33 (2002) 128-136.

E. Damiani, L. Greci. R. Parsons, J. Knowland, Nitroxide radicals protect DNA from damage when illuminated in vitro in the presence of dibenzoylmethne and a common sunscreen ingredient. Free Radic. Biol. Med. 26 (1999) 809-816.

E. Damiani, L. Rosati, R. Castagna, P. Carloni, L. Greci Changes in ultraviolet absorbance and hence in protective efficacy against lipid peroxidation of organic sunscreens after UVA irradiation. J. Photochem. Photobiol.: Biology, Accepted (2005).

A. Deflandre, G. Lang, Photostability assessment of sunscreens. Benzylidene camphor and dibenzoylmethane derivatives. Int. J. Cosmet. Sci. 10 (1988) 53-62.

H. Esterbauer, K.H. Cheeseman, Determination of aldehydic lipid peroxidation products: malodialdehyde and 4 hydroxynonenal, Methods Enzymol.186 (1990) 407-421.

F. Gaboriau, P. Morlière, I. Marquis, A. Moysan, M. Gèze, L. Dubertret, Membrane damage induced in cultured human skin fibroblasts by UVA irradiation, Photochem. Photobiol. 58 (1993) 515-520.

F.P. Gasparro, UV-induced photoproducts of para-aminobenzoic acid, Photodermatol. 2 (1985) 151-157. (abstract only).

F. Gugumus, Photooxidation of polymers and its inhibition, in: J. Pospisil, P.P. Klemchuk (Eds.) Oxidation inhibition in organic materials, vol. II, CRC Press, Boca Raton, FL, 1990, 29-161.

B. Halliwell, J.M.C. Gutteridge, Free Radicals in Biology and Medicine, Oxford University Press, UK (1999) pp. 407-413.

R. Haywood, P. Wardman, R. Sanders, C. Linge, Sunscreens inadequately protect against ultraviolet-A-induced free radicals in skin: implications for skin ageing and melanoma? J. Invest. Dermatol. 121 (2003) 862-868.

R. Jiang, M.S. Roberts, D.M. Collins, H.A.E. Benson, Absorption of sunscreens across human skin: an evaluation of commercial products for children and adults. Br. J. Clin. Pharmacol. 48 (1999) 635-637.

M.C. Krishna, A. Samuni, Nitroxides as antioxidants, Methods Enzymol. 234 (1994) 580-589.

H. Maier, G. Schauberger, K. Brunnhofer, H. Honigsmann, Change of ultraviolet absorbance of sunscreens by exposure to solar-simulated radiation, J. Invest. Dermatol. 117 (2001) 256-262.

P. Morlière, A. Moysan, R. Santus, G. Huppe, J-C. Mazière, L. Dubertret, UVA-induced lipid peroxidation in cultured human fibroblasts, Biochim. Biophys. Acta, 1084 (1991) 261-268.

P. Morlière, A. Moysan, I. Tirache, Action Spectrum for UV-induced lipid peroxidation in cultured human skin fibroblasts, Free Radic. Biol. Med. 19 (1995) 365-371.

S. Pattanaargson, P. Limphong, Stability of octyl methoxycinnamate and identification of its photo-degradation product, Int. J. Cosm. Sci. 23 (2001) 153-160.

A. Samuni, M.C. Krishna, Antioxidant properties of nitroxides and nitroxide SOD mimics, in: L. Packer, E., Cadenas (Eds.) Handbook of Synthetic Antioxidants, Marcel Dekker Inc., New York, 1997, pp. 351-373.

W. Schwack, T. Rudolph, Photochemistry of dibenzoylmethane UVA filters, Part 1, J. Photochem. Photobiol. B. 28 (1995) 229-234.

J. Sedlar, Hindered amines as photostabilizers, in: J. Pospisil, P.P. Klemchuk (Eds.) Oxidation inhibition in organic materials, vol. II, CRC Press, Boca Raton, Fl, 1990, 2-28.

Y. Shu-Xian, H. Xin-yu, H. Yue, L. Kang.huang, Tempol, on of nitroxides, is a novel ultraviolet-A1 radiation protector for human dermal fibroblasts. J. Dermatol. Sci. 37 (2005) 137-143.

S. Simeoni, S. Scalia, H.A.E. Benson, Influence of cyclodextrins on in vitro human skin absorption of the sunscreen, butyl-methoxydibenzoylmethane, Int. J. Pharm. 280 (2004) 163-171.

N. Tarras-Wahlberg, G. Stenhagen, O. Larko, A. Rosén, A-M. Wennberg, O. Wennerstrom, Changes in ultraviolet absorption of sunscreens after ultraviolet irradiation, J. Invest. Dermatol. 113 (1999) 547-553.

L. Zastrow, L. Ferrero, T. Herrling, N. Groth, Integrated sun protection factor: a new sun protection factor based on free radicals generated by UV irradiation, Skin Pharmacol. Physiol., 17 (2004) 219-231.

Alberti, et al, Reactions of indolic nitrons and N-heteroaromatic bases under irradiation and chemical oxidation, New J. Chem., 2003, 27, 1045-1048.

MSDS for compound XP-002434936 1988-2007.

MSDS for compound XP-002434937 1988-2007.

Alberti, et al., New insights into N-tert-butyl-α-phenylnitrone (PBN)† as a spin trap, J. Chem. Soc., Perkins Trans. 2, 1997, 887-892.

Damiani, et al., Nitroxide Radicals Protect DNA From Damage When Illuminated In Vitro in the Presence of Dibenzoylmethane and a Common Sunscreen Ingredient, Free Radical Biology & Medicine, vol. 26, Nos. 7/8, pp. 809-816, 1999.

Damiani, et al., Synthesis and Application of a Novel Sunscreen-Antioxidant, Free Radical Research, May 2006; 40(5): 485-494.

International Search Report, May 25, 2007.

E. Damiani et al.: "Nitroxide radicals protect DNA from damage when illuminated invitro in the presence of dibenzoylmethane and a common sunscreen ingredient." Free Radical Biology and Medicine vol. 26, No. 7/8, 1999, pp. 809-816, XP002434933 XXElsevier Science.

Database Beilstein, Beilstein Institute For Organic Chemistry, Frankfurt-Main, DE; XP002434937 Database accession No. BRN:1488655 & Bull. Acad. Sci. USSR Div. Chem. Sci. 1968, 1997.

Partial European Search Report, Nov. 30, 2009.

E. Damiani et al., "Synthesis and application of a novel sunscreen-antioxidant", Free Radical Research, vol. 40 No. 5, 2006, pp. 485-494, XP008079296.

E. Damiani et al., "Synthesis and application of a novel sunscreen-antioxidant", Free Radical Research, vol. 40, No. 5, 2006, pp. 485-494, XP008079296.

* cited by examiner

SCHEME 1

SYNTHESIS OF A NITROXIDE ANTIOXIDANT AND METHODS OF USE IN COSMETIC AND DERMATOLOGICAL COMPOSITIONS

CROSS-REFERENCE TO RELATED APPLICATIONS

Under 35 U.S.C. §119(e) this application claims the benefit of U.S. Provisional Application No. 60/750,584 filed Dec. 15, 2005, and is hereby incorporated by reference in its entirety.

FIELD OF THE INVENTION

The present invention relates to novel photo absorbing-antioxidant compounds, methods of synthesizing photo absorbing-antioxidant compounds, and their use in dermatological and/or cosmetic compositions. In addition, the present invention relates to the use of methoxycinnamate, and nitroxide compounds for the preparation of a composition for the dermatological and/or cosmetic treatment of skin.

BACKGROUND

It is known that among the most common forms of cancer which affects humans, skin cancer is without doubt one of the most widespread. In particular, in the last twenty years, the incidence of skin cancer has increased remarkably. Part of this increase is due to the fact that, for the typical person, the amount of time exposed to solar radiation, both natural and artificial, has increased. In addition, solar radiation has become less filtered due to the concomitant decreases in the ozone layer. Overexposure of skin to solar radiation has contributed to the increasing use of sunscreens. However, the sunscreens themselves may be subjected to photolytic reactions induced by light, resulting in the formation of free radical species that are harmful to healthy skin.

It is known that the ultraviolet component of solar radiation (UV rays) plays a primary role in inducing skin tumours since these UV rays directly attack cells, damaging their DNA. Owing to the spectral distribution of solar UV, the UVA (380-315 nm) component of sunlight is now believed to be the main cause of photoageing and photocarcinogenesis and is much more effective than UVB (315-280 nm) in inducing peroxidative damage. Consequently, most skin care cosmetic products now include UVA filters in their formulations along with UVB filters, and separately include antioxidants such as vitamin E to deactivate free radicals (e.g., reactive oxygen species (ROS) such as superoxide, hydroxyl, nitric oxide, and peroxyl) generated during UVA exposure.

Modern sunscreens should provide and maintain their initial UV absorbance, and hence protection of skin, throughout the entire period of exposure to sunlight. However, not all UVA and UVB filters are sufficiently photostable. For example, simple in vitro assays show that there is a decrease in the spectral absorbance of most commonly used UV filters and that this largely correlates with increased UVA-induced lipid peroxidation. The magnitude of this effect is affected by the specific UV absorber used, whether it is used alone or in combination, and whether other antioxidants are present.

The addition of antioxidant agents into sunscreen creams is known and in many cases includes categories of compounds such as vitamin E and ascorbic acid. Other antioxidant compounds which have been used for this purpose includes the class of cyclic mono-nitroxide radicals, such as, for example 2,2,6,6-tetramethylpiperidine-1-oxyl (TEMPO), and 2,2,6,6-tetramethylpiperidine-3-hydroxy-1-oxyl (TEMPOL). These are both cyclic aliphatic nitroxides. Another class of antioxidant includes the nitroxide bis(2,2,6,6-tetramethyl-1-oxyl-piperidine-4-yl)sebacate, which appears to be a more efficient photo-antioxidant than vitamin E.

Many cosmetic creams containing sun filters or cosmetic creams which are currently available contain a plurality of antioxidant agents and coformulants. However, the use of antioxidant agents in a cream containing sun filters or in a cream for dermatological and/or cosmetic purposes has various complications and disadvantages.

A first disadvantage is that once applied to the skin some compounds, including antioxidants, could themselves be subjected to degradation due to sun rays with the consequent formation of reactive oxygen species. The free radicals formed are themselves harmful to the skin, cells, and cellular components such as lipids, proteins, and nucleic acids. Furthermore, the free radicals formed can chemically react with other radicals or coformulants present in the sun cream.

Another disadvantage of existing products is due to the fact that when the number of compounds, or antioxidant agents used in a cosmetic cream is increased, it becomes increasingly difficult to prepare a product in which the beneficial characteristics of the compound is stable over time.

Yet another disadvantage of existing products is due to the fact that upon increasing the number of compounds or antioxidant agents used in a cosmetic cream, it becomes increasingly difficult to prepare a product with characteristics of high compatibility in relation to the various skin types on which it will be applied. In fact, it may happen that the topical application of a cream containing a sun filter, or a cosmetic cream, induces certain allergic reactions due to the specific chemical composition of the product.

Furthermore, another disadvantage is that increasing the number of active antioxidant agents used in the preparation of a cream containing a sun filter, or a cosmetic cream, increases the costs of the final product.

Therefore, it would be highly desirable to have at one's disposal a new antioxidant or class of antioxidant compounds that overcomes these disadvantages of the presently utilized products and methods. In particular, it would be desirable to be able to have at one's disposal a single hypoallergenic sunscreen compound that possesses high efficacy UV blocking activity, and antioxidant activity but that is also chemically stable over time.

SUMMARY OF THE INVENTION

The present invention relates to a novel chemical composition useful for the preparation of a dermatological or cosmetic composition for the treatment of skin. The composition and methods of the present invention are suitable for improving the efficacy of photoprotective cosmetic formulations. Therefore, an object of the present invention is to provide a compound for use in cosmetic or dermatological applications that demonstrates improved stability, and improved efficacy in UV absorption and ROS scavenging. As such, in one aspect, the present invention relates to a novel chemical composition that is surprisingly and unexpectedly effective in the prevention of UV-induced photo-oxidative damage. In a preferred embodiment, the invention is a novel chemical compound comprising a combination of a methoxycinnamate linked to a cyclic nitroxide that demonstrates unexpected synergistic activity (i.e., greater than the activity of the respective components in admixture) with respect to UV blocking and ROS scavenging.

Another object of the present invention is to provide a method for synthesizing a compound that demonstrates improved stability, greater UV absorbing, and better ROS scavenging efficiency. One aspect of this object of the invention relates to a method of synthesizing a compound, which demonstrates improved stability, UV absorbing, and ROS scavenging activity, which can be used in cosmetic or dermatological applications for the treatment of skin. In certain of the preferred embodiments the methods comprise covalently linking a UV absorbing moiety, for example OMC (FIG. 1) to a phenolic or cyclic nitroxide moiety capable of free radical scavenging. In certain aspects, the methods of the present invention comprise a step wherein an alkyl group is removed from a methoxycinnamate and replaced with an ROS scavenging phenolic or cyclic nitroxide moiety.

Yet another object of the present invention is to provide a method of using the composition in a dermatological or cosmetic application for the treatment of skin, for example, to treat or prevent UV-induced photo-oxidative damage to skin, cells, or cellular components, for example, lipids, proteins, and nucleic acids of an organism, for example, a human. One aspect of this object comprises administering an effective amount of the composition of the invention in a pharmaceutically acceptable form to an organism in need thereof.

In certain aspects the composition of the invention may be administered together along with any pharmaceutically acceptable carriers, excipients, and/or biologically active or inactive ingredients. Administration of the composition of the invention may be through any suitable dosage form including, for example, creams, lotions, powders, sprays, gels, ointments, a suspension or emulsion, mousses, aerosols, or any one of a variety of transdermal devices for use in the continuous administration of systematically active drugs by absorption through the skin.

Pharmaceutically suitable excipients include, for example, those that improve or prolong delivery, bioavailability, absorption or uptake, shelf-life, stability, solubility, efficacy, viscosity, reduce toxicity, improve taste or smell, and combinations thereof. In any of the preferred embodiments the composition of the invention may optionally include, for example, pharmaceutical compounding agents, such as one or more thickening agents such as paraffin oils, esters such as isopropyl myristate, ethanol, silicone oils and vegetable oils, cellulosic thickening agents, ethylcellulose, hydroxypropyl cellulose, hydroxypropyl methylcellulose, povidone, polyacrylic acids such as carbopol, Sepigel® (polyacrylamide/isoparaffin/laureth-7), the Gantrez® series of polymethyl vinyl ether/maleic anhydride copolymers such as the butyl ester of PVM/MA copolymer Gantrez® A-425, and any thickening agent known in the art that has good compatibility with volatile liquids; a preservative, for example, hydroxybenzoate esters; a glycol; water; a surfactant, such as, ethoxylated fatty alcohols, glycerol mono stearate, phosphate esters, and other commonly used emulsifiers and surfactants; a dermal penetration enhancer, for example, octyl salicylate or DMSO; a reducing agent; an emulsifier; an organic solvent, for example, an ether, an ester, an alcohol or an alkane; a triglyceride; a lipid or phospholipid; an oil; a fat; a carbohydrate or saccharide; a protein; a nucleotide; a liposome; a salt or mineral; a plant extract, and the like. In addition it is also contemplated that in any of the preferred embodiments the composition of the invention can be optionally combined with at least one other active agent including another UV absorbing compound, a drug, for example a hormone, an antimicrobial compound, an anti-inflammatory, an antioxidant, and the like.

Another object of the present invention is to provide a method for synthesizing a cosmetic and/or dermatological composition which includes at least one UV absorbing moiety and at least one moiety capable of scavenging or reducing a reactive free radical species, for example an ROS such as superoxide, hydroxyl, nitric oxide, peroxyl, and combinations thereof.

These as well as other benefits and objects of the present invention will be understood by those of ordinary skill in the art from the following detailed description, and examples of the preferred embodiments.

DESCRIPTION OF THE DRAWINGS OF THE INVENTION

FIG. 1. Chemical formula of compounds. 2-ethylhexyl-4-methoxycinnamate (OMC); 2,2,6,6-tetramethylpiperidine-3-hydroxy-1-oxyl (TEMPOL); 2,2,6,6-tetramethyl-piperidine-4-yl-p-methoxy cinnamyloxy-1-oxyl (MC-NO). SCHEME 1: Example of the method of a preferred embodiment for generating the novel UV-absorbing, ROS scavenging compound of the invention.

FIG. 2. Absorption spectra of 50 µM compounds in acetonitrile. As can be observed, MC-NO has the same spectral profile and extinction coefficient as OMC.

FIG. 3. Absorption spectra of 100 µM compounds before (thick lines) and after (thin lines) exposure to 275 KJ/m2 UVA. See Detailed Description for experimental details.

FIG. 4. Absorbance of TBARS determined in PC multilamellar liposomes (3.5 mM) in PBS, 0.1 mM EDTA, after exposure to 275 KJ/m2 UVA. White bar=no UVA exposure, black bar=UVA exposure, remaining bars=UVA exposure in the presence of 100 µM compounds and the various combinations at the aforementioned concentration.

FIG. 5. Absorbance of TBARS determined in PC multilamellar liposomes (3.5 mM) in PBS, 0.1 mM EDTA, after exposure to 275 KJ/m2 UVA. White bar=no UVA exposure, black bar=UVA exposure, remaining bars=UVA exposure in the presence of 100 µM compounds and the various combinations at the aforementioned concentration.

DESCRIPTION OF THE PREFERRED EMBODIMENTS

The composition of the present invention comprises a compound effective for absorbing UV energy, and scavenging reactive oxygen species for the prevention of UV-induced photo-oxidative damage to the skin, cells, cellular components, for example, proteins, lipids, nucleic acids, and combinations thereof. The unique UV absorbing-antioxidant compound is surprisingly more efficacious in reducing the detrimental effects of UV radiation, and oxygen free radicals than its respective components in simple admixture. In a first preferred embodiment the present invention is a cosmetic or dermatological composition comprising a methoxycinnamate compound of the following general formula (I):

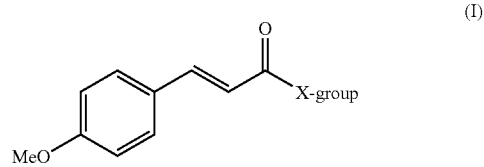

wherein, the X-group comprises a moiety in the category of a phenolic or cyclic nitroxide, for example a piperidine.

In one embodiment, the X-group comprises a moiety of the formula (II):

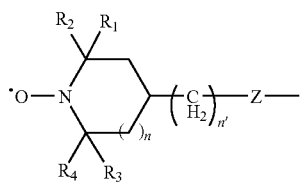

(II)

in which $R_1$, $R_2$, $R_3$ and $R_4$ can be identical or different, each independently represent hydrogen, alkyl, alkenyl, aryl, alkoxy, or —$COOR_5$ with $R_5$ representing an alkyl, alkenyl, aryl or arylalkyl residue; n=0, 1; n'=0-2; and z=—O, —C(O)O, —NH, or —C(O)NH.

In another embodiments the X-group comprises a moiety of the formula (III):

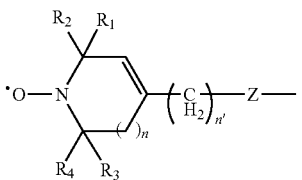

(III)

in which $R_1$, $R_2$, $R_3$ and $R_4$ can be identical or different, each independently represent hydrogen, alkyl, alkenyl, aryl, aralkyl, alkoxy, or —$COOR_5$ with $R_5$ representing an alkyl, alkenyl, aryl or arylalkyl residue; n=0, 1; n'=0-2; and z=—O, —C(O)O, —NH, or —C(O)NH.

In another embodiment the X-group comprises a moiety of the formula (IV):

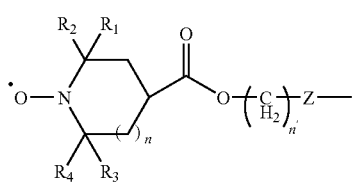

(IV)

in which $R_1$, $R_2$, $R_3$ and $R_4$ can be identical or different, each independently represent hydrogen, alkyl, alkenyl, aryl, aralkyl, alkoxy, or —$COOR_5$ with $R_5$ representing an alkyl, alkenyl, aryl or arylalkyl residue; n=0, 1; n' is an integer greater than or equal to 1; and z=—O, —C(O)O, —NH, or —C(O)NH.

In another embodiment the X-group comprises a moiety of the formula (V):

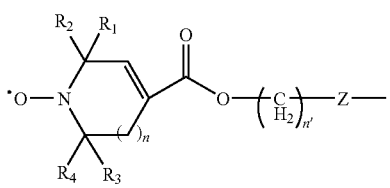

(V)

in which $R_1$, $R_2$, $R_3$ and $R_4$ can be identical or different, each independently represent hydrogen, alkyl, alkenyl, aryl, aralkyl alkoxy, or —$COOR_5$ with $R_5$ representing an alkyl, alkenyl, aryl or arylalkyl residue; n=0, 1; n' is an integer greater than or equal to 1; and z=—O, —C(O)O, —NH, or —C(O)NH.

In another embodiment the X-group comprises a moiety of the formula (VI):

(VI)

in which $R_1$, $R_2$, $R_3$ and $R_4$ can be identical or different, each independently represent hydrogen, alkyl, alkenyl, aryl, aralkyl, alkoxy, or —$COOR_5$ with $R_5$ representing an alkyl, alkenyl, aryl or arylalkyl residue; n=0, 1; n' is an integer greater than or equal to 1; and z=—O, —C(O)O, —NH, or —C(O)NH.

In another embodiment the X-group comprises a moiety of the formula (VII):

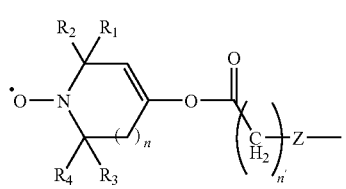

(VII)

in which $R_1$, $R_2$, $R_3$ and $R_4$ can be identical or different, each independently represent hydrogen, alkyl, alkenyl, aryl, aralkyl, alkoxy, or —$COOR_5$ with $R_5$ representing an alkyl, alkenyl, aryl or arylalkyl residue; n=0, 1; n' is an integer greater than or equal to 1; and z=—O, —C(O)O, —NH, or —C(O)NH.

In another embodiment the X-group comprises a moiety of the formula (VIII):

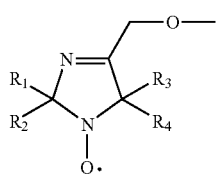

(VIII)

in which $R_1$, $R_2$, $R_3$ and $R_4$ can be identical or different, each independently represent hydrogen, alkyl, alkenyl, aryl, arylalkyl, alkoxy, or —COOR$_5$ with $R_5$ representing an alkyl, alkenyl, aryl or aralkyl residue.

In another embodiment the X-group comprises a moiety of the formula (IX):

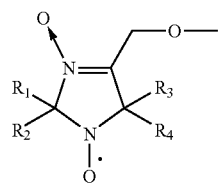

(IX)

in which $R_1$, $R_2$, $R_3$ and $R_4$ can be identical or different, each independently represent hydrogen, alkyl, alkenyl, aryl, aralkyl, alkoxy, or —COOR$_5$ with $R_5$ representing an alkyl, alkenyl, aryl or arylalkyl residue.

In another embodiment the X-group comprises a moiety of the formula (X):

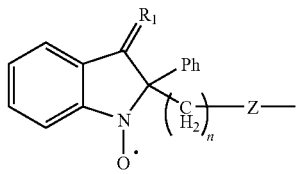

(X)

in which $R_1$ represents an oxygen or a NR$_2$ with $R_2$ representing an alkyl, alkoxy, aryl or phenyl group; n=1, 2, 3; and z=—O, —C(O)O, —NH, or —C(O)NH.

In another embodiment the X-group comprises a moiety of the formula (XI):

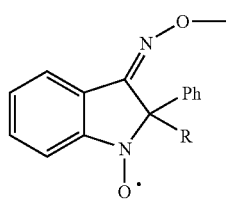

(XI)

in which R represents an alkyl, a phenyl or a substituted benzene residue, a benzylic or a substituted benzylic residue, or an allylic residue.

In another embodiment the X-group comprises a moiety of the formula (XII) or (XIII):

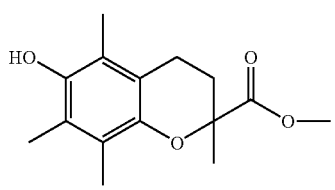

(XII)

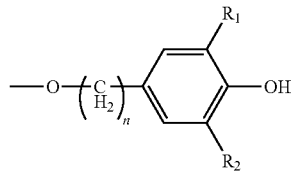

(XIII)

in which $R_1$ or $R_2$ can be a hydroxyl group, a hydrogen, an alkyl or a an alkoxy residue; and n is an integer greater than or equal to 1.

In another embodiment the X-group comprises a moiety of the formula (XIV):

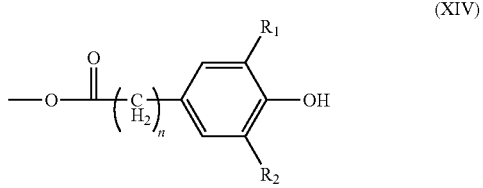

(XIV)

in which $R_1$ or $R_2$ can be a hydroxyl group, a hydrogen, an alkyl or a an alkoxy residue; and n is an integer greater than or equal to 1.

In another embodiment the X-group comprises a moiety of the formula (XV):

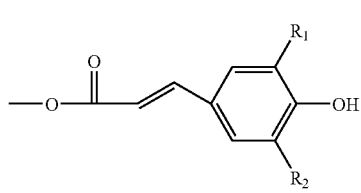

(XV)

in which $R_1$ or $R_2$ can be a hydroxyl group, a hydrogen, an alkyl or an alkoxy residue.

In another of the preferred embodiments, the present invention includes a cosmetic or dermatological composition comprising the UV absorbing-antioxidant of any of the preferred embodiments of the invention, with at least one other active or inactive ingredient.

In a particularly preferred embodiment the composition of the invention comprises a combination of a UV absorbing compound, for example, 2-ethylhexyl-4-methoxycinnamate (OMC), and an antioxidant compound, for example, TEMPOL (4-hydroxy TEMPO). (Scheme 1; FIG. 1). The resulting composition of the invention, 2,2,6,6-tetramethyl-piperidin-4-yl-p-methoxy cinnamyloxy-1-oxyl (MC-NO), retains the 4-methoxycinnamate group responsible for the UV absorbing capacity while the 2-ethylhexyl group responsible for its viscosity has been replaced with a piperidine nitroxide, which has free radical scavenging properties. The new compound may be regarded as a UV-absorbing nitroxide: a novel sunscreen-antioxidant.

The present invention also includes methods for synthesizing a UV absorbing-antioxidant comprising the steps of combining at least one UV absorbing moiety with at least one moiety capable of scavenging or reducing a reactive oxygen species, for example an ROS such as superoxide, hydroxyl, nitric oxide, and peroxyl. Scheme I summarizes one embodiment of the methods of the invention for synthesizing the UV absorbing-antioxidant. Briefly, the method comprises the steps of providing a suitable amount of a methoxycinnamate, dissolving it in methanol in the presence of a catalytic amount of p-toluenesulfonic acid monohydrate. The resulting methoxy methyl cinnamate is dissolved with stoichiometric amounts of a nitroxide, for example, TEMPOL, in toluene with a methanolic solution (8%) of sodium methoxide. The resulting product comprises a UV absorbing methoxycinnamate moiety and an antioxidant nitroxide moiety which, as demonstrated herein, displays improved stability, and greater UV absorbing and ROS scavenging efficiency.

In any of the preferred embodiments the composition of the invention may be administered in any suitable form, together with any pharmaceutically acceptable carriers, excipients, or other biologically active or inactive ingredients. Suitable dosage forms include, for example, creams, lotions, powders, sprays, gels, ointments, suspensions or emulsions, mousses, aerosols, or any one of a variety of transdermal devices for use in the continuous administration of active agents by absorption through the skin.

Pharmaceutically suitable excipients include, for example, those that improve delivery, bioavailability, absorption or uptake, shelf-life, stability, solubility, efficacy, viscosity, reduce toxicity, improve taste or smell, and combinations thereof. In any of the preferred embodiments the composition of the invention may optionally include, for example, pharmaceutical compounding agents, such as one or more thickening agents such as paraffin oils, esters such as isopropyl myristate, ethanol, silicone oils and vegetable oils, cellulosic thickening agents, ethylcellulose, hydroxypropyl cellulose, hydroxypropyl methylcellulose, povidone, polyacrylic acids such as carbopol, Sepigel® (polyacrylamide/isoparaffin/laureth-7), the Gantrez® series of polymethyl vinyl ether/maleic anhydride copolymers such as the butyl ester of PVM/MA copolymer Gantrez® A-425, and any thickening agent known in the art that has good compatibility with volatile liquids; a preservative, for example, hydroxybenzoate esters; a glycol; water; a surfactant, such as, ethoxylated fatty alcohols, glycerol mono stearate, phosphate esters, and other commonly used emulsifiers and surfactants; a dermal penetration enhancer, for example, octyl salicylate; a reducing agent; an emulsifier; an organic solvent, for example, an ether, an ester, an alcohol or an alkane; a triglyceride; a lipid or phopholipid; an oil; a fat; a carbohydrate or saccharide; a protein; a nucleotide; a liposome; a salt or mineral; a plant extract, and the like.

In any of the preferred embodiments, the compound of the invention may be delivered in a cosmetic or dermatological composition in combination with at least one other active agent including another UV absorbing compound, a drug, for example a hormone, an antimicrobial agent, an anti-inflammatory, an antioxidant, and the like.

It is understood that the examples and embodiments described herein are for illustrative purposes only and that various modifications or changes in light thereof will be suggested to persons skilled in the art and are included within the spirit and purview of this application and are considered within the scope of the appended claims. All publications, patents, and patent applications cited herein and in the list of references provided are hereby incorporated by reference in their entirety for all purposes.

In examples of the preferred embodiments, the useful and advantageous synthesis of a UV absorbing-antioxidant is described. The following detailed examples are given by way of example of the preferred embodiments, and are in no way considered to be limiting to the invention. For example, the relative quantities of the ingredients may be varied, additional ingredients may be added, and/or similar ingredients may be substituted for one or more of the ingredients described.

Additional advantageous features and functionalities associated with the systems, methods and processes of the present invention will be apparent from the detailed description which follows. The publications and other materials used herein to illuminate the background of the invention, and in particular cases, to provide additional details respecting the practice of the invention, are incorporated by reference, and for convenience are listed in the appended bibliography.

EXAMPLE #1

Synthesis of 2,2,6,6-tetramethyl-piperidin-4-yl-p-methoxy cinnamyloxy-1-oxyl (MC-NO)

Scheme I shows, in simplified form, an example of an embodiment for the methods of the invention for synthesizing one of the photoabsorbing antioxidants of the invention. In this example, 0.4 mmols of 2-ethylhexyl 4-methoxycinnamate (OMC) is dissolved in 10 ml of methanol in the presence of a catalytic amount of p-toluenesulfonic acid monohydrate. The reaction mixture is refluxed for about 9 hrs, neutralized with 0.5 M $NaHCO_3$, washed with water, and extracted with ethyl acetate. The organic layer is dried over $Na_2SO_4$ anhydrous and the solvent was removed under reduced pressure. A white oil, consisting of p-methoxy methyl cinnamate crystallizing on standing is obtained. In the example above, 4 mmol of OMC yields about 0.5 g (2.5 mmols) of p-methoxy methyl cinnamate.

Next, stoichiometric amounts of TEMPOL, for example 1 mmol (172 mg), and p-methoxy methyl cinnamate (1 mmol, 204 mg) were dissolved in 5 ml of toluene together with 0.1 ml of a methanolic solution (8%) of sodium methoxide. The reaction mixture was refluxed for 5 hrs, and repeatedly washed with water in order to remove the unreacted TEMPOL partially soluble in water. Purification by chromatography ($SiO_2$, 80:20 petroleum ether/diethyl ether) yields about 230 mg (70%) of MC-NO.

Figure 3:
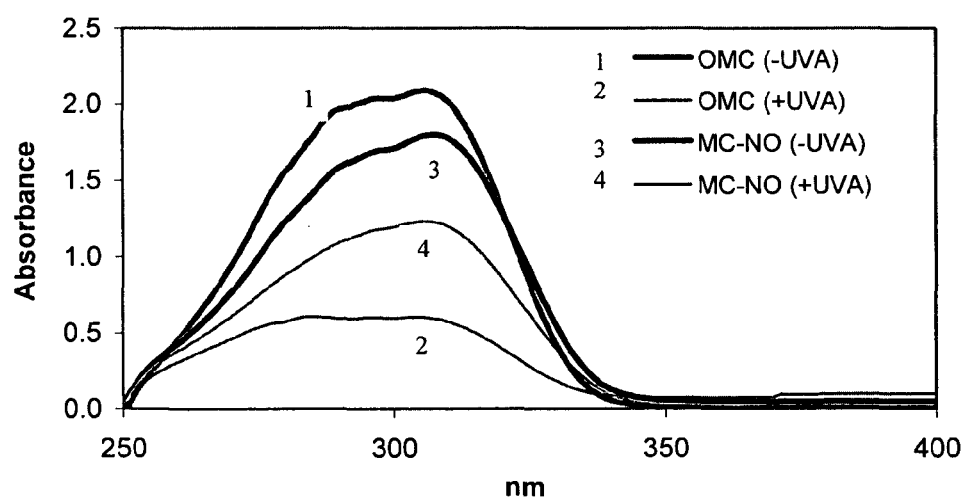
FIG. 3 shows the spectra of MC-NO and OMC before and after exposure to 275 $kJ/m^2$ UVA in buffer and after solvent extraction. The reason for using buffer was to maintain the same medium as the peroxidation experiments so that comparisons between the optical absorption experiments and lipid peroxidation could be meaningful.

As can be seen, there is a strong decrease in spectral absorption for OMC after UV exposure. In fact, this UVB filter has been shown to be light sensitive and a decrease in UV absorption efficiency upon light exposure which results from cis/trans photo-isomerization and possibly [2+2]

cyloaddition at wavelengths above 300 nm, has been reported. The resulting cis-isomer absorbs at the same wavelength, but it has a reduced extinction, thus giving lower spectrophotometric values which could account for the result observed here. Suprisingly, as can be observed in FIG. 3 the decrease in absorbance of MC-NO is not as remarkable as that of OMC alone, implying that the new compound retains the majority of its original absorbance after UVA irradiation. It would appear that the presence of the nitroxide group unexpectedly but advantageously stabilizes the sunscreen.

In the testing described, the present inventors investigated the spectral properties of a new sunscreen-antioxidant, its ability to prevent UVA-induced ROS generation measured as a reduced photo-oxidative damage to lipids and its effect in the presence of the common UVA filter, Parsol 1789.

Figure 4:
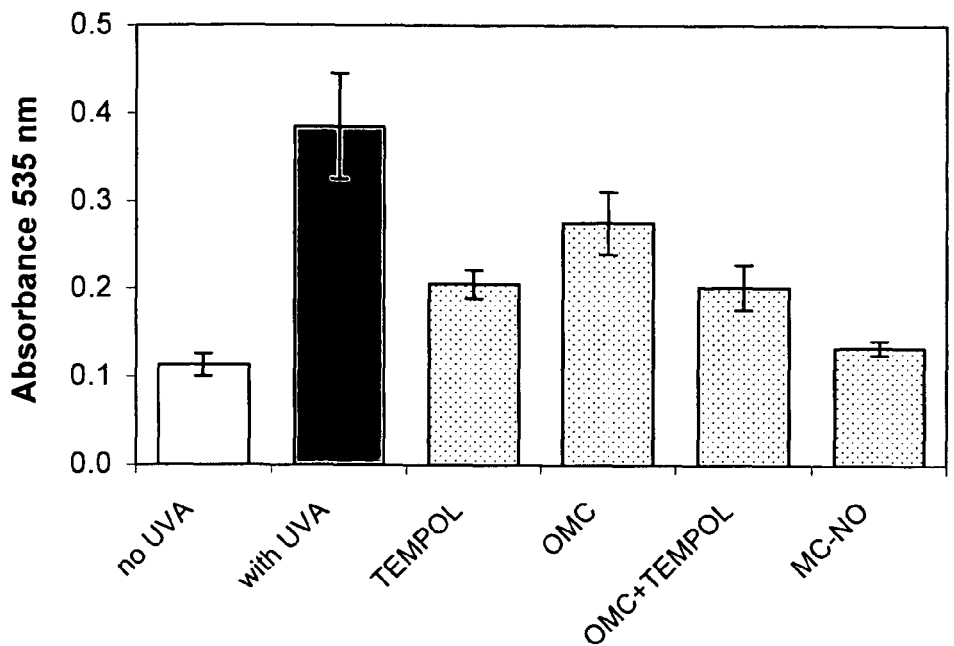

The results on UVA-induced lipid peroxidation were obtained by evaluating the extent of TBARS (thiobarbituric acid reactive substances) formation which mainly arises from the reaction of breakdown products of lipid peroxides, principally malondialdehyde (MDA) with TBA (thiobarbituric acid). MDA is in many instances the most abundant individual aldehyde whose production has been suggested to involve the formation of cyclic peroxides and endoperoxides that undergo fragmentation during lipid peroxidation. Several other compounds (e.g. deoxyribose, methionine, proline, adenosine, DNA) under appropriate conditions also form pink TBA complexes, however in our isolated liposomal system, TBARS can derive only from the breakdown of peroxides formed during PC peroxidation It is known that compared with UVB, UVA generates more oxidative stress, and at levels found in sunlight, it is ten times more efficient than UVB at causing lipid peroxidation leading to plasma membrane damage. Therefore the effects of MC-NO, OMC, TEMPOL and the latter two combined on this oxidative event was studied in vitro using liposomes as membrane models. The extent of the oxidative process was determined through the popular method of evaluating the aldehydic breakdown products (TBARS) produced during lipid peroxidation which absorb at 535 nm, using the TBA assay. FIG. 4 shows the level of absorbance of TBARS measured in liposomal suspensions before and after exposure to 275 kJ/m$^2$ UVA in the absence and presence of tested compounds.

Figure 1:
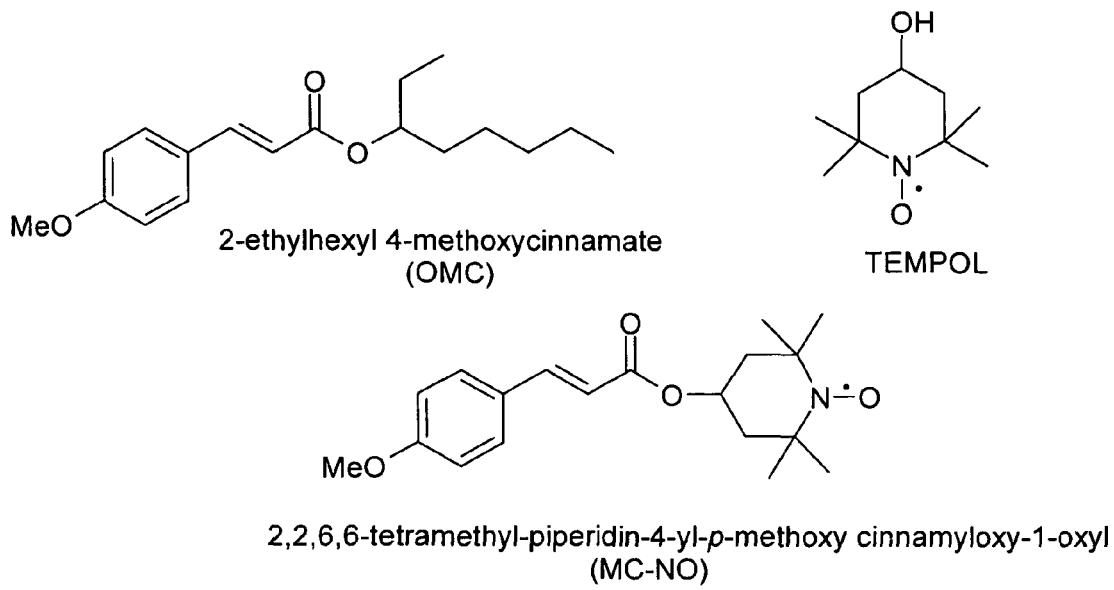
Figure 1:
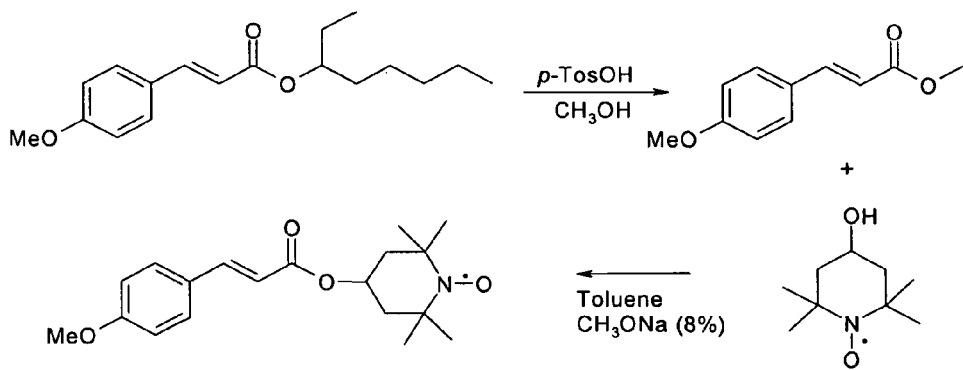
Figure 2:
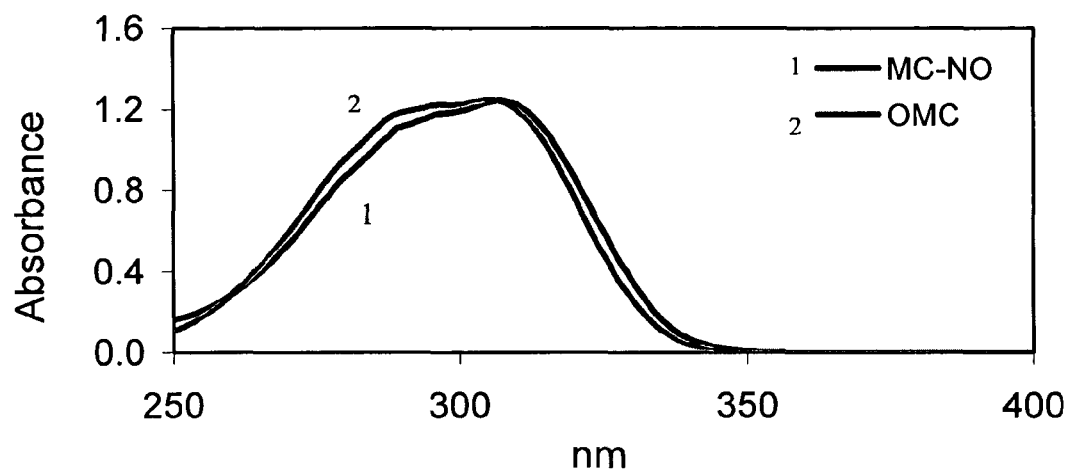
FIG. 2 shows the spectral profile of 50 µM acetonitrile solutions of OMC and MC-NO. As can be observed, the new compound has the same spectral profile and extinction coefficient as OMC.

WVA induces a 3-fold increase in lipid peroxidation in this experimental system. OMC seems to protect UVA-induced lipid peroxidation although it does not absorb in the UVA, except for a very small fraction between 320 and 330 nm. Its spectral behaviour (FIG. 3) shows that there is a decrease in its absorbance which does not necessarily imply photoinstability. OMC undergoes cis/trans isomerization which can be considered a very efficient way of dispersing the absorbed energy and this may explain the protection observed here: part of the UVA energy is attenuated by OMC so less lipids are oxidized. The presence of TEMPOL alone inhibits UVA-induced lipid peroxidation by almost 60%. This is not due to its filtering capacity since it does not absorb in the UVA range but rather to its ability to react with ROS induced by UVA exposure. With the combination OMC/TEMPOL, the reduction in the level of TBARS is the same as that observed with TEMPOL. However, in the samples containing the new compound MC-NO, the level of lipid peroxidation is greatly reduced to almost control levels (non-illuminated control) and this may be due to the fact that the compound is more photostable, as observed in FIG. 2, therefore its protective capacity will be enhanced in addition to the fact that it scavenges UVA-induced free radicals. Noteworthy is the fact that 100 μM of MC-NO is more effective than the combination of 100 μM OMC with 100 μM TEMPOL.

Figure 5:
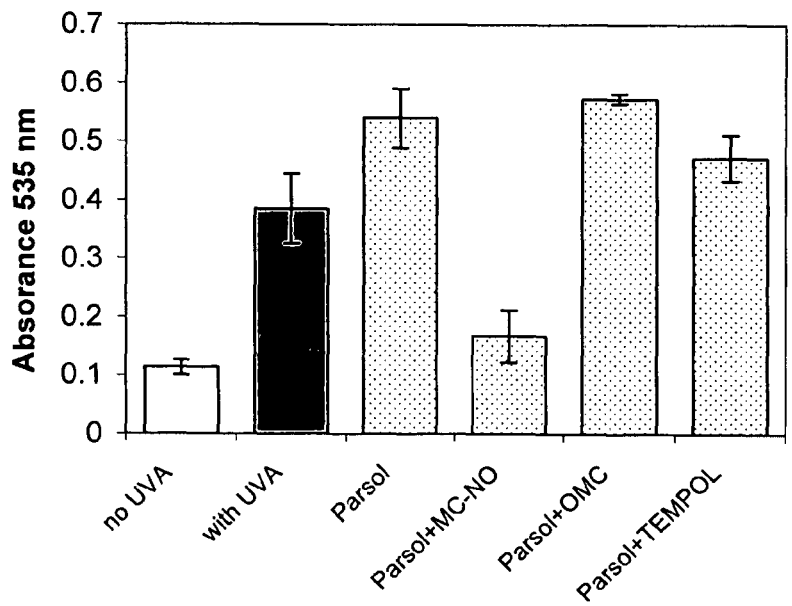

Since the UV-protection spectrum of a sunscreen formulation is usually attained by a mixture of UV-filters, the compatibility between different UV-filters is important. Hence, similar study to that described above was undertaken utilizing the most common UVA filter present on the market, 4-tert-butyl-4'-methoxydibenzoylmethane (commercially known as Parsol 1789 or Avobenzone) which has a high absorptive capacity over almost the entire UVA range. However, this compound has a major drawback because it produces free radicals when activated by UVA that lead to a reduction in photo-protective power and to an increased potential to damage biologically relevant molecules, such as proteins, plasmid DNA and more recently, cultured keratinocytes. The photo-decomposition of sunscreens may hence affect their protection against UV-induced skin damage since their breakdown decreases the UVA absorptive capacity resulting in an increase of the direct UVA-induced skin damage. As can be observed in FIG. 5, the presence of Parsol 1789 leads to a significant increase in the level of absorbance of TBARS compared to the illuminated control, and this result once again confirms that free radicals are produced during UVA illumination of this filter which contributes to exacerbating the free radical chain reaction of lipid peroxidation. In the liposomes containing Parsol/OMC there was no significant difference in lipid peroxidation levels with respect to Parsol alone.

With the combination Parsol/TEMPOL the level of peroxidation compared to Parsol 1789 alone is slightly reduced, however, the level of TBARS reached are higher compared to when TEMPOL is present alone (FIG. 4). This possibly signifies that more radicals are produced when Parsol is present leading to more lipids being oxidized, hence TEMPOL has to scavenge not only the radicals generated by UVA exposure but also those induced by the photo-decomposition of Parsol 1789. The most striking result is the one obtained with the combination Parsol/MC-NO. The presence of 100 μM of the new compound is able to greatly reduce lipid peroxidation to almost control levels when 100 μM of the UVA filter Parsol 1789 is present. This result is believed to be due to the sunscreen-antioxidant properties of the new compound.

The main and immediate damage inflicted by UVA light to cells is produced from free radicals and other oxidative species which may directly or indirectly be responsible for the erythemal reaction too. Understanding the effects of UVA/UVB absorbers and antioxidants upon the level of UV-induced ROS generated under UVA exposure and in natural sunlight, is useful for comprehending the efficacy of skin care cosmetic formulations and may lead to improved photoprotection. This is especially important considering the several reports in the literature which show that UV absorption spectra of sunscreen agents following UVA irradiation are changed in many instances due to photoinstability. Neither the combination of various organic filters nor the addition of inorganic filters seems to guarantee photostability. Recent research by Haywood et al. (2003) also indicates that sunscreen users are little protected against UVA free-radical production and the damaging effects of UVA.

Conclusions

The new UVB-absorbing nitroxide compound leads to a significant reduction in lipid peroxidation (FIG. 4). This is primarily due to the excellent radical scavenging properties of nitroxide radicals. These are a group of compounds whose protective effects in a multiplicity of biological systems at the molecular, cell, organ, and whole-body levels against oxidative stress, have been widely established. The reasons underlying their success is that nitroxides are extremely effective modulators of processes mediated by paramagnetic species (radicals and transition metals) which makes them useful for probing reactions and processes associated with free radicals. In the present description we show that these compounds are also extremely efficient in reducing photo-oxidative damage even in combination with photolabile UV-absorbers. It is worth recalling that nitroxides are derivatives of hindered amine light stabilizers (HALs). These HALs are extensively employed in polymers to prevent photooxidation and their stabilizing effect is attributed to the activity of the nitroxide radical derived from the parent amine as described previously by us. Bernstein et al. have also demonstrated that the nitroxide Tempol affords protection against UV radiation in a transgenic murine fibroblast culture model of cutaneous photoaging, and recently in human dermal fibroblasts too. Therefore these results support the notion that antioxidants, such as nitroxides, may provide useful supplementation to sunscreen protection against photocarcinogenesis and photoaging in skin. However, the novelty of the new nitroxide described herein is that it also has strong UVB-absorbing properties.

This compound is particularly useful since the UVA/free-radical protection currently provided by sunfilters appears to be inadequate. There exists an ongoing requirement for improved cosmetic and dermatological compositions that are efficient UV-blockers, and efficient antioxidants. This is especially true given the fact that human exposure to UV is increasing due to the destruction of the ozone layer, and the use of modern tanning equipment (sunbeds and sunlamps). The novel sunscreen-antioxidant described herein is ideal for reducing the problems associated with photo-induced skin damage.

Detailed Methods

L-α-phosphatidylcholine (P2772: Type XI-E), TEMPOL, 2-ethylhexyl 4-methoxycinnamate (octylmethoxycinnamate; here abbreviated as OMC) as well as all other reagents and solvents were purchased from Sigma-Aldrich Chemical Co. (Milan, Italy). 4-Tert-butyl-4'-methoxydibenzoylmethane (here abbreviated as Parsol) was obtained in the form of Eusolex 9020 from Merck (Darmstadt, Germany) and its identity was confirmed by NMR.

1H NMR spectra were recorded at room temperature in CDCl3 solution on a Varian Gemini 200 spectrometer (δ in ppm referred to tetramethylsilane). ESR spectra were recorded on a Bruker EMX ESR spectrometer equipped with an XL Microwave frequency counter, Model 3120 for the determination of g factors.

As UVA irradiating source, a commercial sun lamp, Philips Original Home Solarium (model HB 406/A; Philips, Groningen, Holland) equipped with a 400 watt ozone-free Philips HPA lamp, UV type 3, delivering a flux of 23 mW/cm2 between 300 and 400 nm, at a distance of 20 cm was used. It was always pre-run for 15 min to allow the output to stabilize. The dose of UVA was measured with a UV Power Pack Radiometer (EIT Inc.).

1H NMR (200 MHz, CDCl3, 25° C., after reduction with phenylhydrazine): δ=1.34 (s, 6H), 1.41 (s, 6H), 1.75-1.91 (m, 2H), 2.00-2.12 (m, 2H), 5.14-5.28 (m, 1H), 6.27 (d, 1H, J=16 Hz), 6.91 (d, 2H, J=8.8 Hz), 7.48 (d, 2H, J=8.8 Hz), 7.63 (d, 1H, J=16 Hz).

ESR spectrum recorded in ethyl acetate (Scheme 1): triplet with $a_N$=15.47 G, g=2.0062$_8$.

Optical Absorption Spectra 10 mM Stock solutions of TEMPOL and the photoactive ingredients were prepared in acetonitrile. Appropriate amounts were then added to 5 mM phosphate buffer, 0.9% NaCl, 0.1 mM EDTA, pH 7.4 (acetonitrile<2% v/v) and mixed thoroughly to reach final concentrations of 100 μM in a final volume of 3 ml. The solutions were then transferred to a 24 multi-well plate for cell cultures (Orange Scientific, Cambrex BioScience, Walkerville, Inc.) which was placed on a brass block embedded on ice at a distance of 20 cm from the light source. The multi-well plate was covered with a 2 mm thick quartz slab to prevent any evaporation. The incident dose of UVA received from above by the samples was 275 kJ/m$^2$. After illumination, 2.4 ml of sample were collected from each well and extracted with the same volume of ethyl acetate. The organic phase was separated and its absorption spectrum was then run on a UV Kontron 941 spectrophotometer. For the non-illuminated samples, the same procedure was followed for the same length of time except that the samples were exposed to direct artificial laboratory working light.

Peroxidation of Multilamellar Phosphatidylcholine (PC) Liposomes Induced by UVA

PC multilamellar liposomes were prepared as follows. The desired amount of egg PC in chloroform was added to a glass test-tube kept in an ice bath and the solvent was thoroughly removed under a stream of nitrogen. When compounds were to be tested, either alone or in combination, the desired amount of an acetonitrile solution of the compound/s was introduced into another glass test-tube and after solvent evaporation, egg PC was added and subjected to the same procedure as described above. The lipid films prepared were each dispersed in 1.5 ml of 5 mM phosphate buffer, 0.9% NaCl, 0.1 mM EDTA, pH 7.4 and vortexed for 2 min until a white, homogeneous, opalescent suspension was obtained. The final concentration of PC in the resulting multilamellar liposomal dispersion was 3.5 mM. Each sample was then aliquoted into 2 parts (700 μl each) and transferred into a multi-well plate, covered with a 2 mm thick quartz slab to prevent any evaporation and exposed to UVA as described above. The incident dose of UVA-received from above by the samples was 275 kJ/m$^2$. At the end of UVA exposure, the extent of lipid peroxidation was assessed using a modified method of the thiobarbituric acid (TBA) assay.[14] In this procedure, 2 ml of TBA-TCA-HCl (0.375% w/v TBA, 15% w/v TCA, 0.2 M HCl) was added to 600 μl of sample containing BHT 0.3 mM to prevent possible peroxidation of liposomes during the TBA assay. The samples were heated for 15 min at 95° C. followed by cooling and centrifugation. The absorbance of the pink chromophore of the supernatant developed upon heating, was measured at 535 nm.

2,2,6,6-tetramethyl-piperidin-4-yl-p-methoxy cinnamyloxy-1-oxyl (here abbreviated MC-NO) was synthesized from commercial 4-hydroxy-2,2,6,6,-tetramethyl-piperidine-1-oxyl (TEMPOL) and the methyl ester of p-methoxy cinnamic acid. The typical procedure (Scheme 1) requires the reactants to be refluxed in toluene for 4-5 hrs in the presence of sodium methoxide as catalyst, as reported in the literature (I. Dragutan, *Free Rad. Res. Comms.* 1990, 9, 379-382)

Appropriate controls were carried out throughout all the experiments described above and the results reported are an average of at least three independent experiments each performed in duplicate.

In examples of the preferred embodiments, a method is described for the generation of a novel and useful UV-absorbing and ROS scavenging compound. The detailed examples are given by way of example of the preferred embodiments, and are in no way considered to be limiting to the invention. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the detailed description.

REFERENCES

The following references are hereby incorporated into the present disclosure by reference, in their entirety and for all purposes.

[1] E. Damiani, L. Rosati, R. Castagna, P. Carloni, L. Greci Changes in ultraviolet absorbance and hence in protective efficacy against lipid peroxidation of organic sunscreens after UVA irradiation. J. Photochem. Photobiol.: Biology, Accepted (2005).

[2] E. Damiani, P. Carloni, C. Biondi, L. Greci, Increased oxidative modification of albumin when illuminated in vitro in the presence of a common sunscreen ingredient: protection by nitroxide radicals, Free Radic. Biol. Med. 28 (2000) 193-201.

[3] E. Damiani, L. Greci. R. Parsons, J. Knowland, Nitroxide radicals protect DNA from damage when illuminated in vitro in the presence of dibenzoylmethne and a common sunscreen ingredient. Free Radic. Biol. Med. 26 (1999) 809-816.

[4] T. Armeni, E. Damiani, M. Battino, L. Greci, G. Principato, Lack of in vitro protection by a common sunscreen ingredient on UVA-induced cytotoxicity in keratinocytes, Toxicology, 203 (2004) 165-178.

[5] E. Damiani, R. Castagna, L. Greci, The effects of derivatives of the nitroxide TEMPOL on UVA-mediated in vitro lipid and protein oxidation, Free Radic. Biol. Med. 33 (2002) 128-136.

[6] H. Maier, G. Schauberger, K. Brunnhofer, H. Honigsmann, Change of ultraviolet absorbance of sunscreens by exposure to solar-simulated radiation, J. Invest. Dermatol. 117 (2001) 256-262.

[7] J. Knowland, P. J. McHugh, R. Dunford, The photochemical potential of some sunscreens to damage DNA, in: F. P. Gasparro (Ed.) Sunscreen Photobiology. Molecular, Cellular and Physiological Aspects, Springer-Verlag, Berlin, 1997, pp. 47-68.

[8] J. M. Allen, C. J. Gosset, A. K. Allen, Photochemical formation of singlet molecular oxygen in illuminated aqueous solutions of several commercially available sunscreen ingredients, Chem. Res. Toxicol. 9 (1996) 605-609.

[9] F. P. Gasparro, UV-induced photoproducts of para-aminobenzoic acid, Photodermatol. 2 (1985) 151-157.

[10] N. M. Roscher, M. K. O. Lindeman, S. B. Kong, C. G. Cho, P. Jiang, Photodecomposition of several compounds commonly used as sunscreen agents. J. Photochem. Photobiol. A. 80 (1994) 417-421.

[11] A. Deflandre, G. Lang, Photostability assessment of sunscreens. Benzylidene camphor and dibenzoylmethane derivatives. Int. J. Cosmet. Sci. 10 (1988) 53-62.

[12] Y. Shu-Xian, H. Xin-yu, H. Yue, L. Kang.huang, Tempol, on of nitroxides, is a novel ultraviolet-A1 radiation protector for human dermal fibroblasts. J. Dermatol. Sci. 37 (2005) 137-143.

[13] E. F. Bernstein, S. K. Kong, D. B. Brown, B. C. Kwak, T. Takeuchi, F. P. Gasparro, J. Uitto, The nitroxide TEMPOL affords protection against ultraviolet radiation in a transgenic murine fibroblast culture model of cutaneous photoaging, Exp. Dermatol., 10 (2001) 55-61.

[14] J. Buege, S. D. Aust, Microsomal lipid peroxidation, Methods Enzymol. 52 (1978) 302-310.

[15] N. Tarras-Wahlberg, G. Stenhagen, O. Larko, A. Rosén, A-M. Wennberg, O. Wennerstrom, Changes in ultraviolet absorption of sunscreens after ultraviolet irradiation, J. Invest. Dermatol. 113 (1999) 547-553.

[16] J. K. Broadbent, B. S. Martincigh, M. W. Raynor, L. F. Salter, R. Moulder, P. Sjoberg, K. E: Markides, Capillary supercritical fluid chromatography combined with atmospheric pressure chemical ionisation mass spectrometry for the investigation of photoproduct formation in the sunscreen absorber 2-ethylhexyl-p-methoxycinnamate, J. Chromatography A, 732 (1996) 101-110.

[17] S. Pattanaargson, P. Limphong, Stability of octyl methoxycinnamate and identification of its photo-degradation product, Int. J. Cosm. Sci. 23 (2001) 153-160.

[18] P. Morlière, A. Moysan, R. Santus, G. Huppe, J-C. Mazière, L. Dubertret, UVA-induced lipid peroxidation in cultured human fibroblasts, Biochim. Biophys. Acta, 1084 (1991) 261-268.

[19] P. Morlière, A. Moysan, I. Tirache, Action Spectrum for UV-induced lipid peroxidation in cultured human skin fibroblasts, Free Radic. Biol. Med. 19 (1995) 365-371.

[20] F. Gaboriau, P. Morlière, I. Marquis, A. Moysan, M. Gèze, L. Dubertret, Membrane damage induced in cultured human skin fibroblasts by UVA irradiation, Photochem. Photobiol. 58 (1993) 515-520.

[21] H. Esterbauer, K. H. Cheeseman, Determination of aldehydic lipid peroxidation products: malodialdehyde and 4 hydroxynonenal, Methods Enzymol. 186 (1990) 407-421.

[22] W. Schwack, T. Rudolph, Photochemistry of dibenzoylmethane UVA filters, Part 1, J. Photochem. Photobiol. B. 28 (1995) 229-234.

[23] M. A. Pathak, M. Carbonare, Reactive oxygen species in photoaging and biochemical studies in the amelioration of photoaging changes, in: F. Urbach (Ed.) Biological responses to ultraviolet A radiation, 1992, pp. 189-207.

[24] Tyrell R. M. UVA (320-380 nm) radiation as an oxidative stress, in: H. Sies (Ed.) Oxidative stress: oxidants and antioxidants, Academic Press, San Diego, 1991, pp. 57-83.

[25] A. Cantrell, D. J. McGarvey, Photochemical studies of 4-tert-butyl-4-methoxydibenzoylmethane (BM-DBM), J. Photochem. Photobiol. B. 64 (2001) 117-122.

[26] I. Andrae, A. Bringhen, F. Boehm, H. Gonzenbach, T. Hill, L. Mulroy, T. G. Truscott, A UVA filter (4-tert-butyl-4methoxydibenzoylmethane): photoprotection reflects photophysical properties, J. Photochem. Photobiol. B. 37 (1997) 147-150.

[27] R. Haywood, P. Wardman, R. Sanders, C. Linge, Sunscreens inadequately protect against ultraviolet-A-induced free radicals in skin: implications for skin ageing and melanoma? J. Invest. Dermatol. 121 (2003) 862-868.

[28] B. Halliwell, J. M. C. Gutteridge, Free Radicals in Biology and Medicine, Oxford University Press, UK (1999) pp.407-413.

[29] J. B. Mitchell, M. C. Krishna, A. Samuni, Nitroxides as protectors against oxidative stress, in: C. Colton, D. Gilbert (Eds.) Reactive Oxygen Species in Biological Systems, Plenum Press, New York, 1997, pp. 293-313.

[30] A. Samuni, M. C. Krishna, Antioxidant properties of nitroxides and nitroxide SOD mimics, in: L. Packer, E., Cadenas (Eds.) Handbook of Synthetic Antioxidants, Marcel Dekker Inc., New York, 1997, pp. 351-373.

[31] M. C. Krishna, A. Samuni, Nitroxides as antioxidants, Methods Enzymol. 234 (1994) 580-589.

[32] F. Gugumus, Photooxidation of polymers and its inhibition, in: J. Pospisil, P. P. Klemchuk (Eds.) Oxidation inhibition in organic materials, Vol. II, CRC Press, Boca Raton, Fla., 1990, 29-161.

[33] J. Sedlar, Hindered amines as photostabilizers, in: J. Pospisil, P. P. Klemchuk (Eds.) Oxidation inhibition in organic materials, Vol. II, CRC Press, Boca Raton, Fla., 1990, 2-28.

[34] L. Zastrow, L. Ferrero, T. Herrling, N. Groth, Integrated sun protection factor: a new sun protection factor based on free radicals generated by UV irradiation, Skin Pharmacol. Physiol., 17 (2004) 219-231.

[35] G. Potard, C. Laugel, H. Schaefer, J-P-Marty, The stripping technique: in vitro absorption and penetration of five UV filters on excised fresh human skin, Skin Pharmacol. Appl. Skin Physiol. 13 (2000) 336-344.

[36] R. Jiang, M. S. Roberts, D. M. Collins, H. A. E. Benson, Absorption of sunscreens across human skin: an evaluation of commercial products for children and adults. Br. J. Clin. Pharmacol. 48 (1999) 635-637.

[37] S. Simeoni, S. Scalia, H. A. E. Benson, Influence of cyclodextrins on in vitro human skin absorption of the sunscreen, butyl-methoxydibenzoylmethane, Int. J. Pharm. 280 (2004) 163-171.

[38] K. Herzog, K. Sommer, W. Baschong, J. Roeding, Nanotopes™, a surfactant resistant carrier system, SOFW Journal 124 (1998) 614-623.

We claim:

1. A chemical composition comprising a methoxycinnamate compound of the general formula (1)

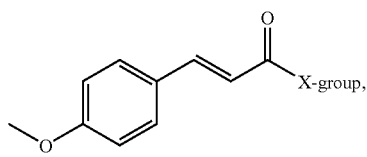

(I)

wherein the X-group comprises:

(i) a moiety of formula (II) or (III)

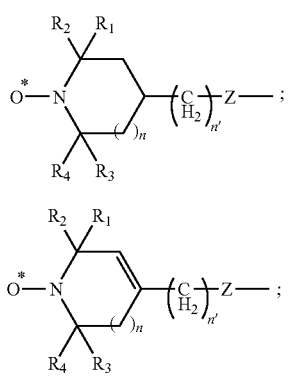

(II)

(III)

wherein $R^1$, $R^2$, $R^3$ and $R^4$ can be identical or different, each selected from the group consisting of hydrogen, alkyl, alkenyl, aryl, aralkyl, alkoxy, and —$COOR^5$, wherein $R^5$ is selected from the group consisting of an alkyl, alkenyl, aryl and an arylalkyl residue; and wherein n is 0 or 1; n' is 0, 1, or 2; and z is a member from the group consisting of —O, —C(O)O, —NH, and —C(O)NH; or (ii) a moiety of formula (IV) or (V)

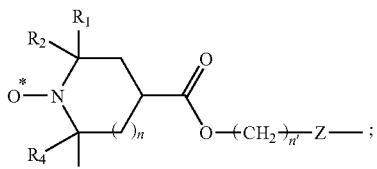

(IV)

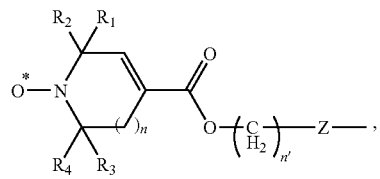

(V)

wherein $R^1$, $R^2$, $R^3$ and $R^4$ can be identical or different, each selected from the group consisting of hydrogen, alkyl, alkenyl, aryl, aralkyl, alkoxy, and —$COOR^5$ sherein $R^5$ is selected from the group consisting of an alkyl, alkenyl, aryl, and an arylalkyl residue; and wherein, n is 0 or 1; n' is an integer greater than or equal to 0; and z is a member from the group consisting of —O, —C(O)O, —NH, and —C(O)NH; or (iii) a moiety of formula (VI) or (VII):

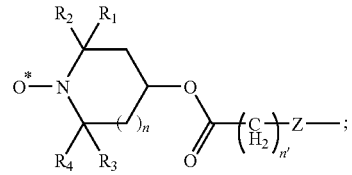

(VI)

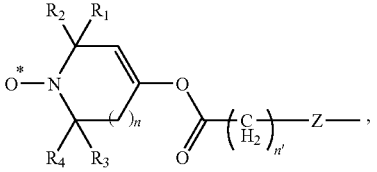

(VII)

wherein $R^1$, $R^2$, $R^3$ and $R^4$ can be identical or different, each selected from the group consisting of hydrogen, alkyl, alkenyl, aryl, aralkyl, alkoxy, and —$COOR^5$ wherein $R^5$ is selected from the group consisting of an alkyl, alkenyl, aryl or arylalkyl residue; and wherein n is 0 or 1; n' is an integer greater than or equal to 0; and z is a member selected from the group consisting of —O, —C(O)O, —NH, and —C(O)NH; or (iv) a moiety of formula (VIII) or (IX):

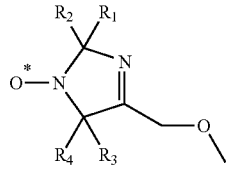

(VIII)

-continued

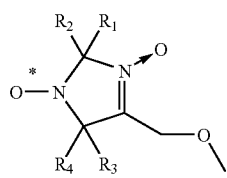
(IX)

wherein $R^1$, $R^2$, $R^3$ and $R^4$ can be identical or different, and selected from the group consisting of hydrogen, alkyl, alkenyl, aryl, aralkyl, alkoxy, and —COOR$^5$ wherein $R^5$ is selected from the group consisting of an alkyl, alkenyl, aryl, and an aralkyl residue; or (v) a moiety of formula (X):

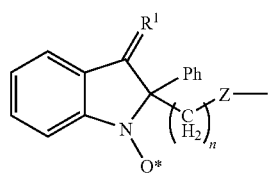
(X)

wherein $R^1$ represents an oxygen or a $NR^2$, and $R^2$ represents a member selected from the group consisting of an alkyl, an alkoxy, an aryl, and a phenyl group; and n is 1, 2 or 3; and Z is a member selected from the group consisting of —O, —C(O)O, —NH, and —C(O)NH; or (vi) a moiety of formula (XI)

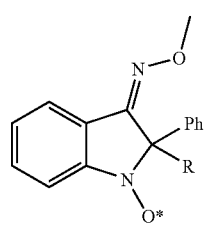
(XI)

wherein R represents a member selected from the group consisting of an alkyl, a phenyl, a substituted benzene residue, a benzylic or a substituted benzylic residue, and an allylic residue; or (vii) a moiety of formula (XII)

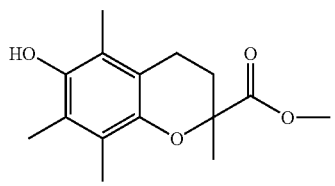
(XII)

(viii) a moiety of formula (XIII)

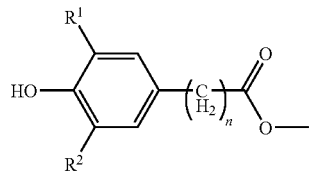
(XIII)

wherein $R^1$ and $R^2$ can be identical or different, each selected from the group consisting of a hydroxyl group, a hydrogen, an alkyl, and an alkoxy residue; and n is an integer greater than or equal to 1; or (ix) a moiety of formula (XIV)

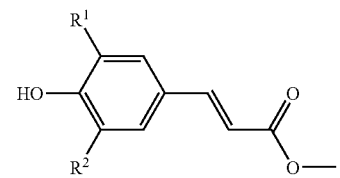
(XIV)

wherein $R^1$ and $R^2$ can be identical or different, each selected from the group consisting of a hydroxyl group, a hydrogen, an alkyl, and an alkoxy residue.

2. The composition of claim 1, wherein the composition further includes at least one other ingredient selected from the group consisting of a pharmaceutically acceptable excipient, a pharmaceutical compounding agent, a preservative, a glycol, a water, a surfactant, an emulsifier, a dermal penetration enhancer, a reducing agent, an organic solvent, an antioxidant, a triglyceride, a lipid or phospholipid, an oil, a fat, a carbohydrate or saccharide, a protein, a nucleotide, a liposome, a salt or mineral, a plant extract, an active agent, and combinations thereof.

3. The composition of claim 2, wherein the composition comprises a pharmaceutically suitable form selected from the group consisting of a cream, a lotion, a powder, a spray, a gel, an ointment, a suspension or emulsion, a mousse, an aerosols, and a transdermal device.

* * * * *